United States Patent [19]

Jeutter et al.

[11] Patent Number: 5,069,210

[45] Date of Patent: Dec. 3, 1991

[54] COCHLEAR IMPLANT EMPLOYING FREQUENCY-DIVISION MULTIPLEXING AND FREQUENCY MODULATION

[76] Inventors: Dean C. Jeutter; Fabien J. Josse, both of 1515 W. Wisconsin Ave., Milwaukee, Wis. 53233; James C. Han, 1057 E. 5600 South, Salt Lake City, Utah 84121

[21] Appl. No.: 339,479

[22] Filed: Apr. 17, 1989

[51] Int. Cl.⁵ .............................................. A61N 1/36
[52] U.S. Cl. .................................. 128/420.6; 455/41
[58] Field of Search ............. 128/420.5, 420.6, 419 R; 455/41; 600/25

[56] References Cited

U.S. PATENT DOCUMENTS

| | | | |
|---|---|---|---|
| 4,592,359 | 6/1986 | Galbraith | 128/419 R |
| 4,611,598 | 9/1986 | Hortmann et al. | 128/419 R |
| 4,741,339 | 5/1988 | Harrison et al. | 128/419 PS |
| 4,918,745 | 4/1990 | Hutchison | 455/41 |

*Primary Examiner*—Lee S. Cohen
*Assistant Examiner*—Kevin Pontius

*Attorney, Agent, or Firm*—Pravel, Gambrell, Hewitt, Kimball & Krieger

[57] ABSTRACT

A cochlear prosthesis composed of a transmitter part which is to be carried exterior to the user's body and a receiver part which is to be implanted in the user, the transmitter and receiver parts being coupled by a radio link provided by implanted receiver coils and external transmitter coils free of any percutaneous connections. In the transmitter part, sound signals are obtained in plurality of channels, and these channels are frequency multiplexed into a composite signal with the aid of a plurality of surface acoustic wave filters, each having a respective passband. In the implanted receiver, the received composite signal is frequency demultiplexed by means of a similar plurality of surface acoustic wave filters each having a respective passband. A further signal is transmitted from the transmitter part to the receiver part via the radio link in order to supply operating power for the circuits in the receiver part, where the further signal is rectified to produce d.c. operating voltages.

6 Claims, 7 Drawing Sheets

COCHLEAR IMPLANT EMPLOYING FREQUENCY-DIVISION MULTIPLEXING AND FREQUENCY MODULATION

BACKGROUND OF THE INVENTION

The present invention relates to hearing aids having an implantable part, and particularly cochlear prosthetic devices with no percutaneous connections.

Radiolinked cochlear prosthetic devices which operate in conjunction with hearing aids and speech processors utilizing digital encoding and time division multiplexing have been reported. These systems can suffer from loss of transmitter/receiver synch due to a rf link drop out, insufficient audio amplitude resolution, and limited audio bandwidth. Transcutaneous speech signal transmission systems utilizing ultrasound and modulated infra red light have also been reported with attendant difficulties of the need for coupling gels, accurate and stable alignment of transducers, and impractically large power requirements.

SUMMARY OF THE INVENTION

It is an object of the present invention to provide an improved cochlear prosthetic device which eliminates or minimizes many of the drawbacks of previously proposed devices.

A specific object of the invention is to provide improved transmission of sound information to an implanted receiver portion of such a device.

Another object of the invention is to provide a transcutaneous transmission link which is free of any percutaneous connections.

A further object of the invention is to supply sound signals having high amplitude resolution and audio frequency bandwidth.

Another object of the invention is to provide a device of the above-mentioned type having reduced power requirements.

The above and other objects are achieved, according to the present invention, by a cochlear prosthesis comprising:

a transmitter part arranged to be carried by a user and comprising: a sound-to-electrical signal transducer for deriving an electrical analog signal representative of incident acoustic signals in the audible frequency range; sound processing means connected to the transducer for dividing the electrical analog signal into a plurality of component signals; frequency modulating means connected to the sound processing means for deriving a plurality of frequency modulated signals each having a respectively different center frequency and each frequency modulated with a respective component signal; bandpass filter means composed of a plurality of first filter elements, each element being connected to receive a respective frequency modulated signal from the frequency modulating means and having a selected pass band centered on a respective center frequency of the frequency modulating means; frequency multiplexing means connected to the filter means for combining the signals passed by all of the filter elements; and transmitting antenna means connected to the frequency multiplexing means for emitting a radiation signal corresponding to the signals combined by the frequency multiplexing means; and a receiver part arranged to be surgically implanted in the user's body and comprising: receiving antenna means arranged to be positioned in proximity to the transmitting antenna means for converting the radiation signal emitted by the transmitting antenna means into a received signal corresponding to the signals combined by the frequency multiplexing means; frequency demultiplexing means including a plurality of second filter elements, the frequency demultiplexing means being connected to the receiving antenna means for causing each second filter element to pass a respective portion of the received signal lying in a respective frequency band; demodulator and amplifier means connected to the frequency demultiplexing means for individually demodulating and amplifying the signal portion passed by each second filter element; and a plurality of output electrodes each arranged to be implanted at a selected location in a cochlea of the user and each connected to the amplifier means for receiving a respective individually amplified received signal portion.

DESCRIPTION OF THE PREFERRED EMBODIMENTS

Figure 1:
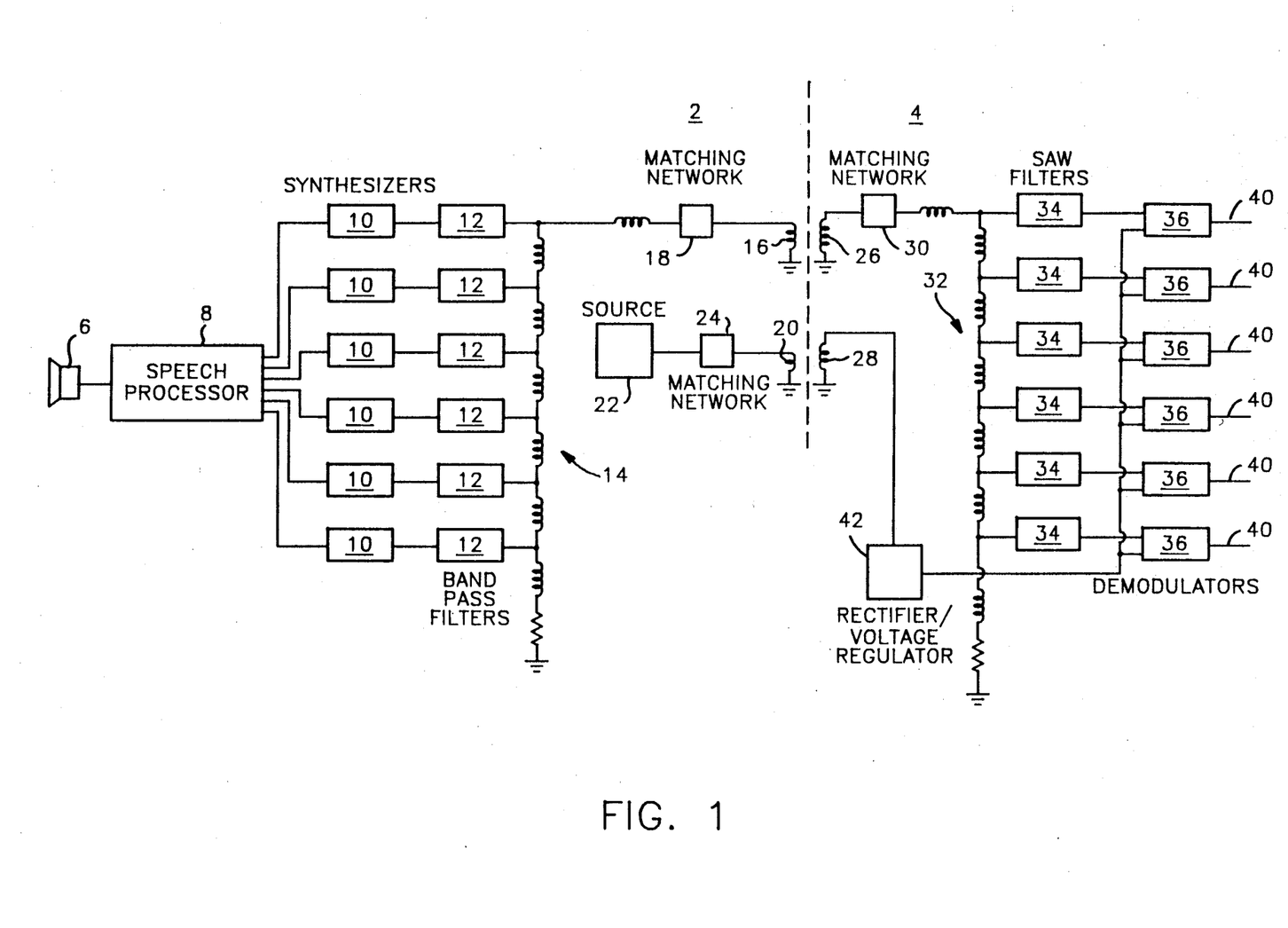
FIG. 1 is a block circuit diagram of a preferred embodiment of a prothesis according to the present invention.

FIG. 1 illustrates a complete system according to the invention, which includes a transmitter portion 2 and a receiver portion 4. Transmitter portion 2 includes a microphone 6 connected to a speech processor 8 which divides the sound signal supplied by microphone 6 into six signal channels. Processor 8 could be constituted by a known speech processor, such as a device marketed by Symbion, Inc., under the trademark Ineraid Sound Processor. Processor 8 separates the sound signal provided by microphone 6 into six frequency bands.

Each output channel of processor 8 is connected to a respective radio frequency FM synthesizer, or modulator, 10, which frequency modulates a respective carrier frequency signal with the information signal appearing on the associated output line of processor 8. The center frequencies of the carrier signals associated with the six synthesizers vary, in the illustrated embodiment, between 72 and 78 MHz, with a frequency spacing of 1.2 MHz.

The frequency modulated output signal from each synthesizer 10 is supplied to a respective surface acoustic wave (SAW) band pass filter 12 of a filterbank tuned to the center frequency of the carrier wave of the associated synthesizer 10. Each synthesizer 13 has a band width of the order of 0.5 MHz. The outputs of all filters 12 are coupled to a series arrangement of inductors 14 to form a constant-k ladder network, which has a low input VSWR. The output end of this network is connected to a first output coil 16 via an amplifying and matching network 18. The center frequency of the signal supplied to coil 16, in the illustrated embodiment, is in the vicinity of 75 MHz.

Transmitter portion 2 further includes a second output coil 20 connected to a source 22 via a matching network 24 of a further signal at a fixed frequency, for example 10 MHz, the signal applied to coil 20 representing a source of operating power for receiver portion 4.

Receiver portion 4 includes a secondary composed of a coil 26 inductively coupled to coil 16 and a coil 28 inductively coupled to coil 20. Coil 26 is connected, via a matching network 30, to a demultiplexer composed of a bank of SAW filters 34 connected, like the arrangement in portion 2, to a series arrangement of inductors 32 to form a constant-k ladder network. The demultiplexer divides the received signal into the original six channels, each of which is supplied to a respective demodulator and electrode driver circuit 36. The output of each demodulator 36 is connected to respective electrode 40 implanted in the cochlea.

In accordance with the invention, each demodulator 36 is preferably constituted by a direct conversion FM receiver, which offers the advantage of structural simplicity and can be composed of an rf amplifier, a frequency discriminator, an audio amplifier and a current source output.

Operating power for demodulators 36 is provided from secondary coil 28 via a suitable rectifier and voltage regulator network 42.

Figure 2:
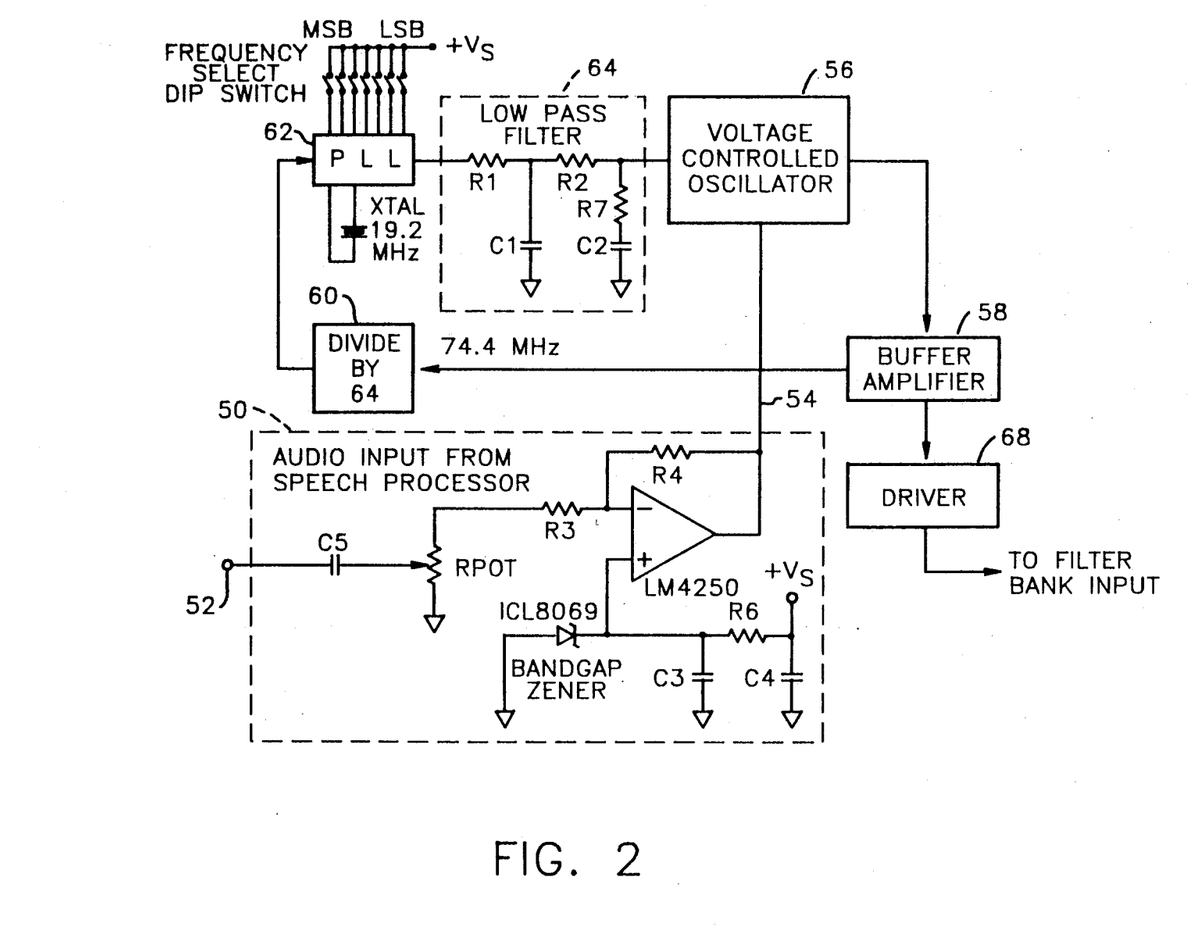
FIG. 2 is a block circuit diagram of one component of the device of FIG. 1.

A preferred embodiment of a radio frequency FM synthesizer 10 which can be employed in each channel of the transmitting portion of a system according to the present invention is illustrated in FIG. 2.

The synthesizer includes an input stage 50 having an input terminal 52 connected to one channel of the speech processor. Input stage 50 performs a conventional amplifying operation and includes a bandgap Zener reference to provide a temperature stable dc component in the amplified voltage supplied to line 54. The synthesizer further includes a control loop composed of a voltage controlled oscillator 56, a buffer amplifier 58, a frequency divider 60, a phase locked loop 62 and a low pass filter 64. The loop is operative for causing voltage controlled oscillator 56 to generate an output signal which is frequency modulated by the audio signal appearing at line 54 and which has the center frequency of one of the transmitter channels. The output signal from oscillator 56 is amplified in buffer amplifier 58 and then conducted via a driver amplifier 68 as the synthesizer output signal to one filter bank input. The output from buffer amplifier 58 is additionally supplied to frequency divider 60 which, in the exemplary embodiment, divides the frequency of the signal produced by oscillator 56 by 64, the frequency divided signal being applied to phase locked loop 62.

Phase locked loop 62, which is crystal controlled by a crystal having an operating frequency of 19.2 MHz, is provided with a set of frequency selection DIP switches which will be set before the system is placed into operation in accordance the center frequency of the particular channel in which the synthesizer is connected. In the embodiment illustrated in FIG. 2, the DIP switches will be set to give loop 62 a reference frequency equal to 74.4/64 MHz.

Thus, loop 62 will produce an error output whenever the frequency of the signal supplied to divider 60 differs from 74.4 MHz. The error output signal from loop 62 is supplied to the control input of oscillator 56 via a low pass filter 64 which is preferably a passive second order low pass filter optimized for response time, i.e., damping. Thus, the control signal applied to oscillator 56 is responsive only to variations in the average value of the oscillator output frequency and, in particular, is insensitive to frequency variations produced by the speech signal supplied to oscillator 56 via line 54.

Voltage controlled oscillator 56 may be a Colpitts type oscillator which is frequency modulated by both the error voltage supplied from loop 62 via filter 64 and the amplified audio signal supplied via line 54.

A practical embodiment of the invention was constructed with a modulation sensitivity of 250 KHz deviation for 200 mVpp audio input amplitude. The frequency modulated VCO output was buffered and amplified to a level of 12 dBm into a 50Ω load. Modulation bandwidth was 50 Hz to 10 KHz. The second and third harmonics were −50 and −46 dBc respectively. Power consumption per channel at 5 VDC supply voltage was 180 mW. Temperature coefficient of frequency was 0.14 ppm/°C.

Figure 3:
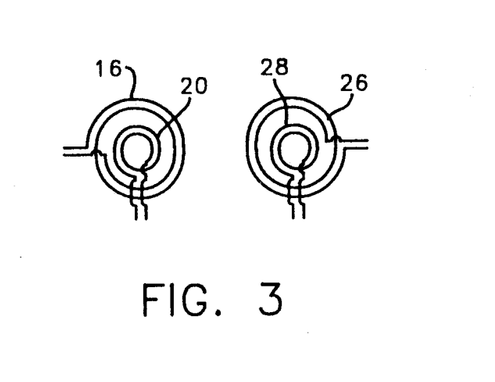
FIG. 3 is a pictorial view of radio linking coils employed in the device of FIG. 1.

A preferred form of construction for the transcutaneous transmission coils 16, 20, 26 and 28 is illustrated in FIG. 3. The external coil pair 16, 20 and the internal coil pair 26, 28 are each constituted by a coplanar pair of circular, concentric coils potted in epoxy for support. Each coil 16 and 26 is constituted by two turns of AWG 24 wire and each coil 20 and 28 may be constituted by two or three turns of AWG 24 wire. Coil 16 had a diameter of 2.54 cm, coil 20 a diameter of 2 cm, coil 26 a diameter of 2 cm and coil 28 a diameter of 1.6 cm. Preferably, primary coils 16 and 20 are series tuned and secondary coils 26 and 28 are parallel tuned by suitably selected capacitors. It has been found that this form of construction provides efficient power transfer and tolerance to reasonable misalignment. The coils are arranged to establish a spacing of the order 5±2 mm between the primary and secondary coils, while allowing for possible misalignments arising from axial separation, transverse offset, and angular displacements.

Coils 16 and 20 are tuned by series capacitances, while coils 26 and 28 are tuned by shunt capacitances. The coils of each pair have a common connection to the reference, or ground, potential for the respective circuit unit.

Figure 4:
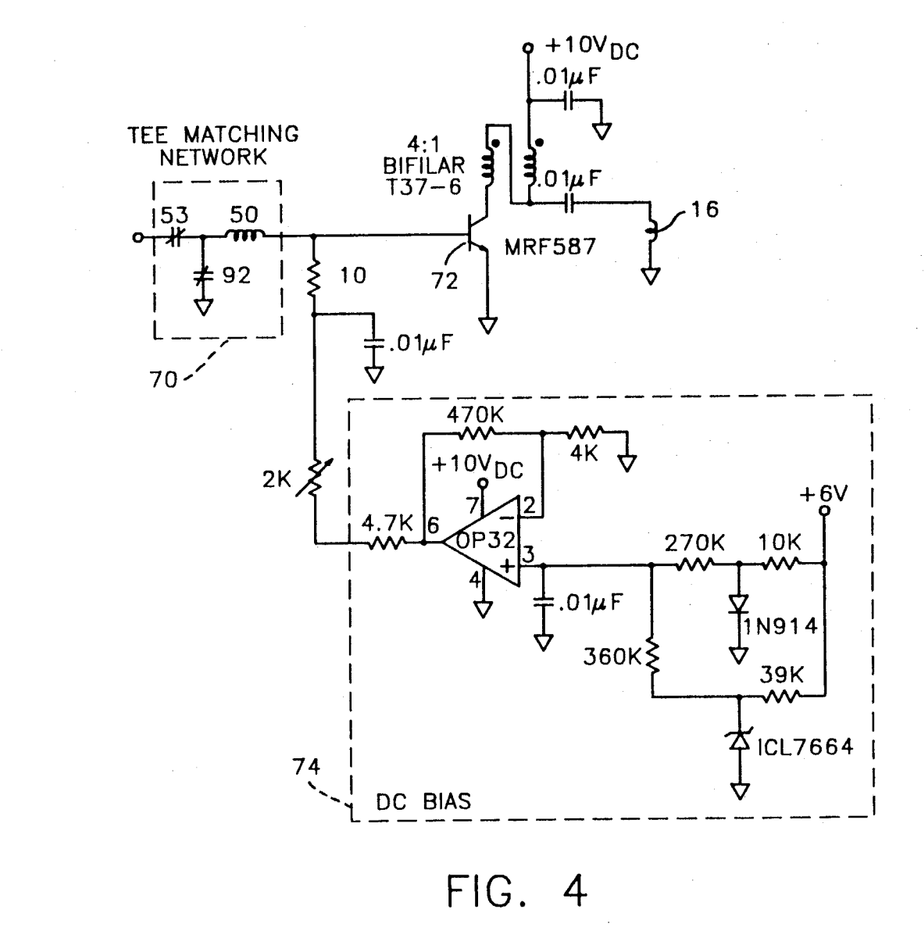
FIGS. 4, 5, 6 and 7 are circuit diagrams of various components of the device of FIG. 1.

A preferred embodiment of matching and linear amplifier network 18 is the depicted in FIG. 4. This includes a Tee matching network 70 which matches the input impedance of an amplifying transistor 72 to the output impedance of filterbank 12, 14. In order to achieve optimum results, it has been found that a signal level of the order of 10 dBm should be supplied to primary winding 16. This requires a highly linear power amplification and for this purpose, transistor 72 is an ultralinear transistor such as a type MRF587 bipolar transistor. The output of transistor 72 is coupled to coil 16 via a matching network which includes a 4:1 bifilar T37-6 transformer.

Transistor 72 is biased by an adjustable DC bias circuit 74 containing a micropower opamp device which incorporates a bandgap Zener reference as shown in FIG. 4. Bias circuit 74 is biased to place amplifier 72 into class A operation. The illustrated circuit has been found to provide a gain of 13 dB with IMD at −55 dBc, measured with the six carrier channels active and one channel unmodulated.

Reverting to FIG. 1, matching network 30 can be a passive π matching network which matches the output impedance of coil 26 to the input impedance of demultiplexer 32, 34.

The 6-channel SAW filterbank 32, 34 with the custom developed filters described above is incorporated into the receiver circuits as a front-end frequency selection device. The "common" input port of the SAW filterbank is appropriately matched to the internal 72-78 MHz patient coil 26 using $\pi$-section lowpass network 30. Composite input level is nominally 10 dBm, with an expected variation of ±3 dB due to coil misalignments, into the 50Ω filterbank input. The separated data channel outputs, at about −13 dBm, are supplied unmatched to individual signal inputs of circuits 36.

Figure 5:
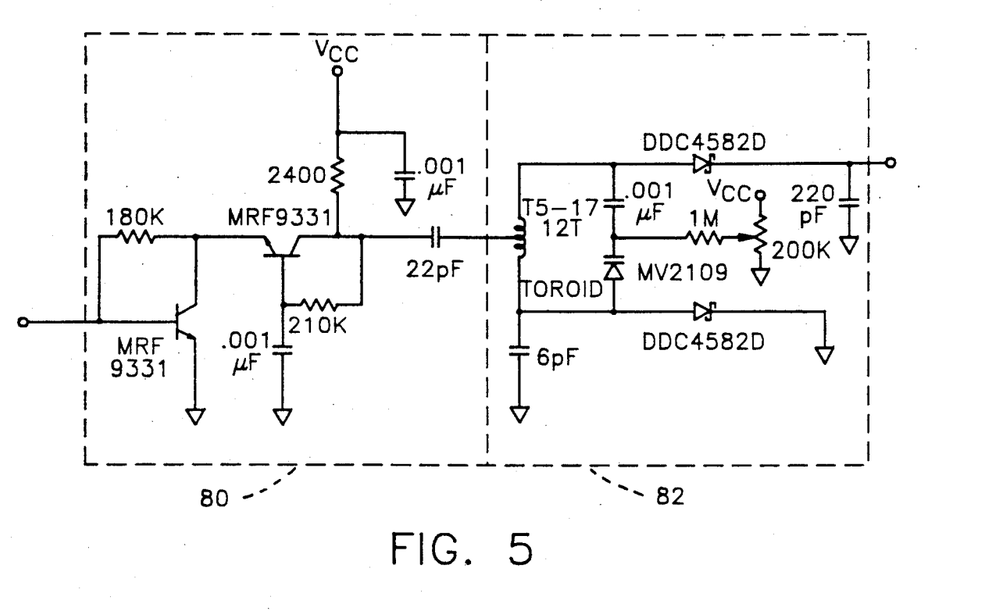
Figure 6:
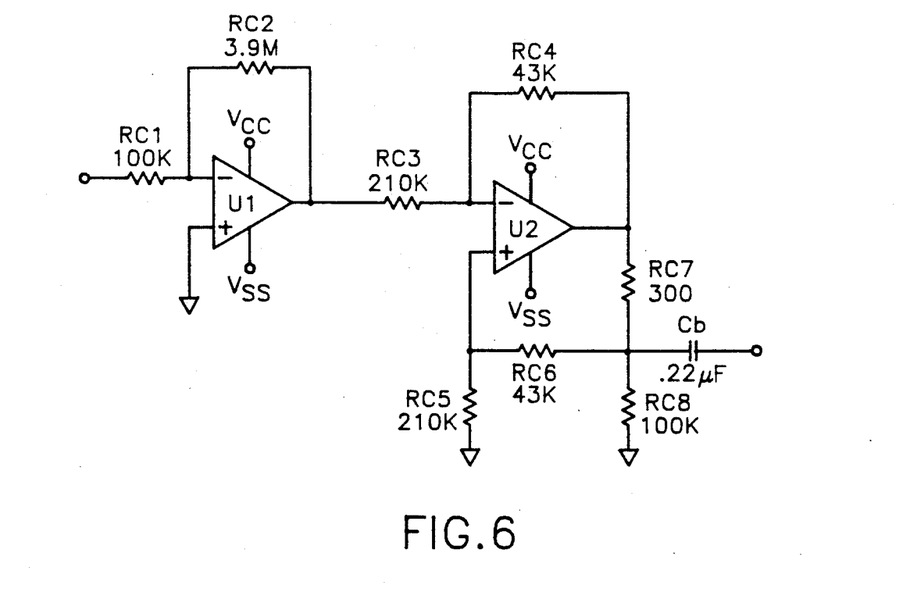

An embodiment of one circuit 36 is shown in FIGS. 5 and 6. Direct conversion FM receivers were chosen for simplicity in implementation as micropower hybrid microcircuits and include a demodulator (FIG. 5) composed of an rf amplifier 80, and a frequency discriminator 82, and an electrode driver (FIG. 6) composed of an audio amplifier, and current source output to properly supply patient cochlear electrodes. Rf amplifier 80 is a cascode configuration of two micropower MRF9331 bipolar transistors. The circuit exhibits high input impedance and the low output impedance required to drive the frequency discriminator, and requires 550 μA at 6 VDC. Discriminator circuit 82 uses a conventional quadrature arrangement of L and C elements with beam lead zero bias Schottky diodes (Alpha DDC4582D) and a varactor diode tuning (MV2109). The inductor is driven at its center tap and is wound with AWG 40 copper wire on a 5 mm diameter torodial powdered iron core. Varactor tuning of the circuit allows for ready adjustment by resistor trimming in the microcircuit implementation. The tuned circuit Q was chosen to provide low audio distortion, the audio output level of the circuit is 20 mVpp, and bandwidth extends from 0 to over 40 KHz.

As shown in FIG. 6, the audio amplifier includes a micropower opamp U1 which amplifies the voltage from discriminator 82, obtaining the needed gain at the requisite 100 Hz to 8 KHz audio bandwidth. This amplifier is followed by a current source connected output stage having a micropower opamp U2. The output level supplies a bipolar signal of 6 Vpp into a 10KΩ resistive load at the full 250 KHz FM deviation.

In further accordance with the invention, operating power, i.e., $V_{ss}$ and $V_{cc}$, is supplied to receiver part 4 by a second radio link. For this purpose, unit 22 in transmitter part 2 is composed of a power oscillator and amplifier generating a 10 MHz output signal at the requisite power level. In the system described thus far, the receiver system shown in FIGS. 5 and 6 requires 36 mW of regulated power.

Ten MHz was selected because any generated harmonics would conveniently lay at frequencies below (70 MHz) and above (80 MHz) the band of data frequencies and therefore not cause harmonic or IMD interference. The 10 MHz power is generated using a MRF581 bipolar transistor with Class C bias. The stage is driven by a single stage crystal controlled oscillator and is appropriately matched via a $\pi$-section lowpass network 24 to the primary 20 of the 10 MHz transcutaneous patient coil. Received power is rectified in device 42 using Schottky diodes in half wave configurations to provide both positive and negative 6 VDC after subsequent regulation by CMOS regulators. An exemplary embodiment of device 42 is shown in FIG. 7.

Figure 7:
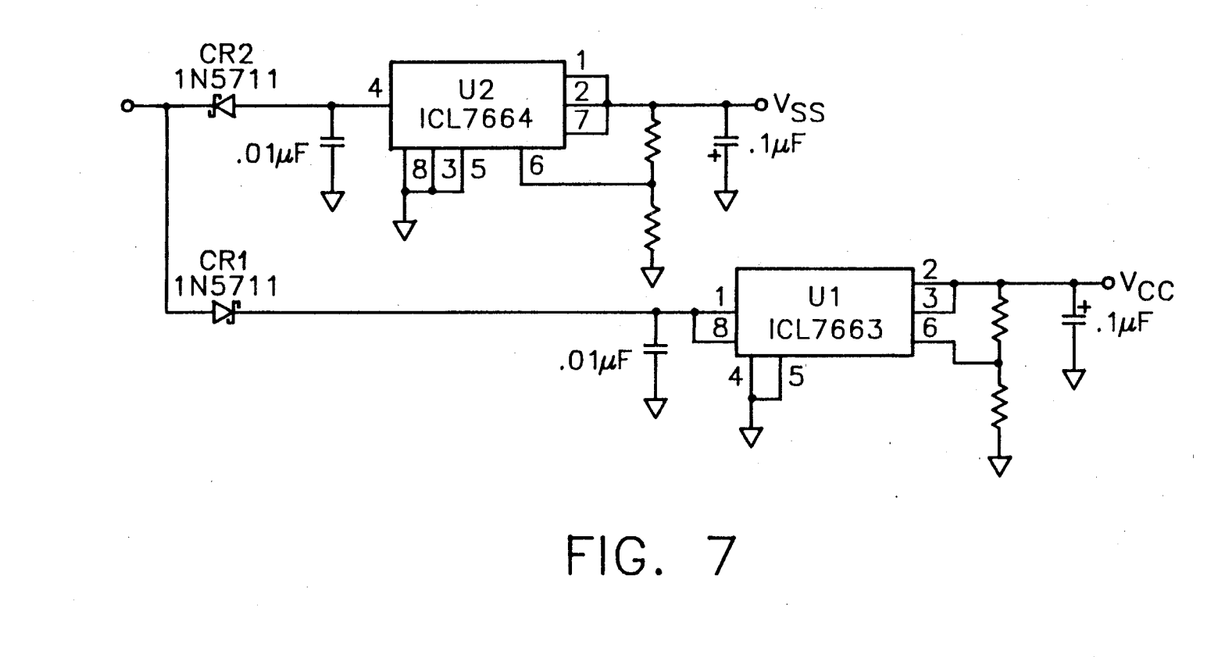

FIGS. 5, 6 and 7 will be seen to identify exemplary component types and values.

Referring now to SAW filters 12 and 34, the size of the filterbank particularly in receiver portion 4, was of primary concern. The passbands of the individual SAW Filters are centered at 72, 73.2, 74.4, 75.6, 76.8, and 78 MHz, each with a 3 dB bandwidth of 0.5 MHz (i.e.: fractional bandwidth of approximately 0.7%). The device specifications are summarized in Table 2. Note that there is an additional specification which is the SAW individual channel filter size. These specifications indicate that the SAW filterbank must be both compact and efficient.

TABLE 2

| Specifications for Individual SAW Filter | |
|---|---|
| Center Frequency, MHz | 72.0, 73.2, 74.4, 75.6, 76.8, 78.0 |
| Bandwidth (−3 dB) | 0.5 MHz |
| Fractional Bandwidth | 0.64 to 0.69% |
| Transition Bandwidth | 0.22 MHz at −40 dB |
| | 0.25 MHz at −60 dB |
| Rejection | ≧50 dB |
| Passband Ripple | 0.5 to 1.0 dB |
| Phase Ripple | 1 to 5 Degrees |
| Shape Factor | 1.88 |
| Substrate | ST-cut Quartz |
| Device Size: | |
| Length | 21 mm |
| Width | 4.5 mm |
| Untuned Insertion Loss | ≦20 dB |

Because of the restriction in size, a simple two-transducer structure has been used for the SAW filters, with one unweighted and one weighted transducer, based on the impulse response technique. The individual filters were designed using a numerical Fourier Transform technique that leads to a closed form synthesis procedure and to the interdigital electrode apodization function of finite extent (i.e., a truncated finite impulse response).

In this technique, the desired frequency response was approximated by translated, nearly triangular eigenfunctions, which have a good sidelobe rejection (>60 dB). The eigenfunction was selected from the family of the $\cos^\alpha(x)$ (F. J. Harris "On the Use of Windows for Harmonic Analysis With Discrete Fourier Transform", proceedings of the IEEE, vol. 66, no. 1, pp. 51-83, 1978) windows and is given in the time domain by $$W(t,T) = \begin{cases} 0.44 + 0.5\cos 2\pi t/T + 0.07\cos 4\pi t/T, & |t| \leq T/2 \\ 0, & |t| > T/2 \end{cases}$$

where T is the filter time length which depends on the filter transition bandwidth.

For example, for the channel centered at 74.4 MHz, the time length, T, of the apodized functions is T=8.4 μs. Three eigenfunctions were used for the synthesis. This translates into about 626 finger pairs in the apodized transducer alone. To complete the synthesis requires a wideband unweighted transducer which has 124 finger pairs. This translates into a device about 35 mm long on ST-cut quartz. It would result in a filterbank whose individual channel response has sidelobe level greater than 67 dB. However, because the present application requires a much smaller device at the selected frequencies, further truncation of the finite impulse response was required. To eliminate higher sidelobes, minimize passband broadening and other second order effects caused by the additional truncation of the finite impulse response, a unique technique involving both analytical and numerical methods was used to modify the overlap length of the remaining electrodes of the apodized transducer. This technique consists of truncating the function h(t,T), which represents the apodized transducer weighting function, to the desired size, then "modulating" each sample of the remaining function (i.e., the weighted electrodes of the interdigital transducer) by a corresponding sample of a carefully selected window function, $W_1(t,T_1)$ of time length $T_1$ such that $T_1 < T$. The new function representing the new apodized transducer is denoted as $h_1(t,T_1)$ where each ith sample:

$$H_1(t_i,T_1) = h(t_i,T) \cdot W_1(t_i,T_1)$$

Note that the sampling intervals of h(t,T) and $W_1(t,T_1)$ are identical.

The window functions $W_1(t,T_1)$ used here consist of the modified cosine squared windows such as Blackman or the Blackman-Harris window, etc., or their combination. Finally, the number of samples in the unapodized transducer is then slightly readjusted to achieve the best possible response at the desired size.

Because of the very narrow fractional bandwidth (<0.7%) of each channel, the devices were designed and fabricated on ST-cut quartz which is also a temperature stable crystal orientation. Several correction factors were included in the design and implementation to achieve the optimized design filters. "Split-electrode" configuration was used to eliminate end electrode reflections and metal grating between the input and output transducer was used to lower RF feedthrough and passband ripple due to velocity difference between metalized and unmetalized surfaces. Velocity correction was also obtained by adjusting the electrode metal thickness.

The 6-channel SAW filterbank was then synthesized by combining the individual SAW filters in a constant-k ladder network, an approach which is both efficient and has a low input VSWR. This is done after each IDT equivalent circuit has been analyzed. The transducers were modeled using superposition analysis techniques generally used for weak piezoelectric coupling material such as quartz.

In the above-described practical embodiment, a relatively high sidelobe level was present, partly due to direct feedthrough resulting from the chosen close spacing between input and output IDT. However, the achieved dynamic range of 40 dB will still meet the required system performance.

Since the filterbank was terminated at 50Ω, the value of the inductances of the constant-k line may be calculated as $Z_0 = (L/C)^{\frac{1}{2}}$ which corresponds to $$L = Z_0^2 C = 100 \ nH \text{ and } \frac{L}{2} = 50 \ nH$$

The network was implemented using chip inductors and chip resistors for miniaturization purposes. The overall per channel insertion loss is 23 dB which includes about 3 dB for the terminated constant-k ladder network.

Figure 8:
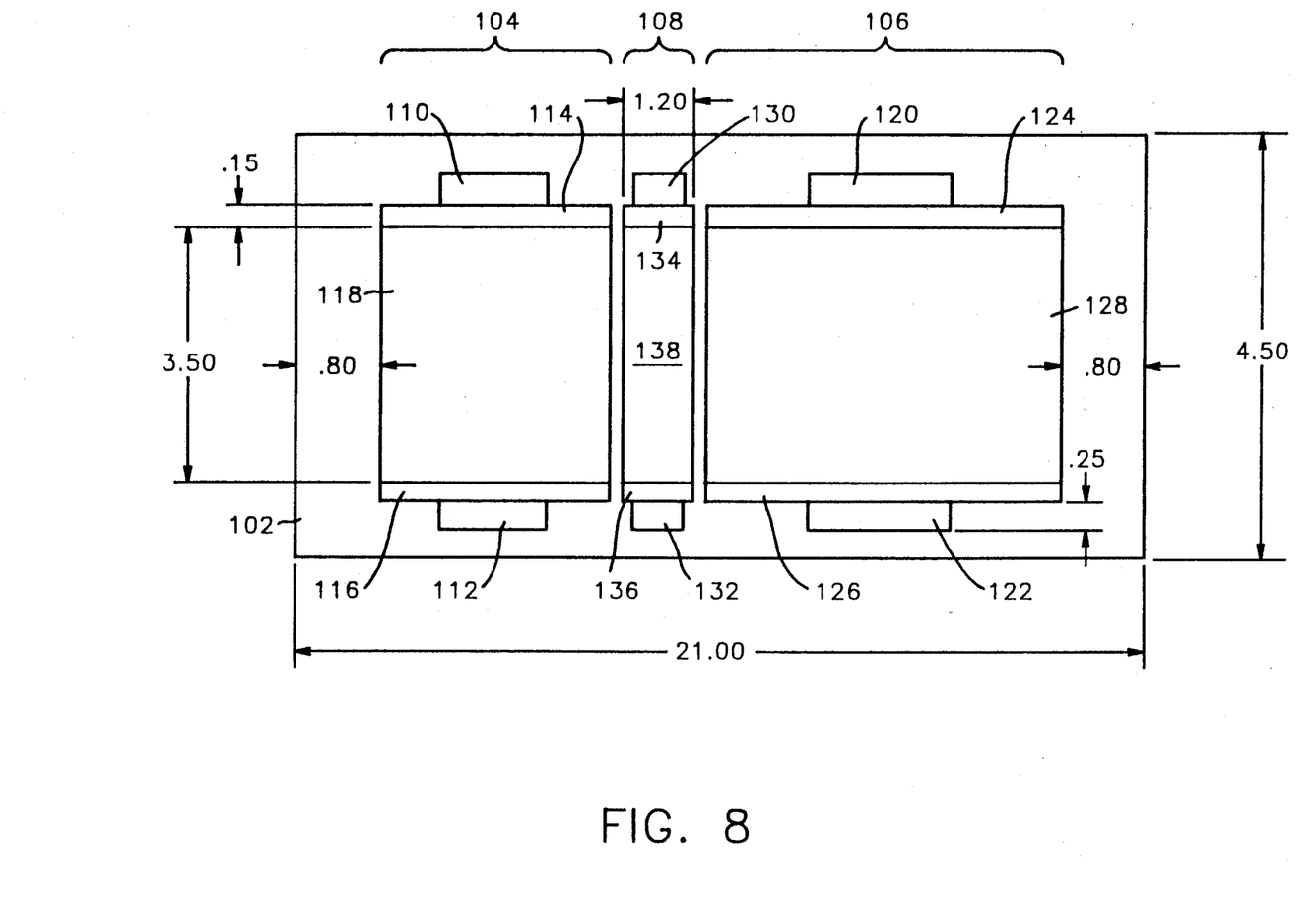
FIG. 8 is a plan view of one embodiment of a surface acoustic wave device employed in the embodiment of FIG. 1.

The overall arrangement of an exemplary SAW filter which may constitute a filter 12 in one transmitter channel or a filter 34 in one receiver channel is shown in FIG. 8. This filter includes a planar substrate 102 made of ST-cut quartz and having a thickness of 0.8 mm. On substrate 102 there is deposited a metal electrode structure having a thickness of $1 \times 10^{+3}$ Å. The metal structure includes an input transducer 104, an output transducer 106 and an isolating member 108. All relevant dimensions of an exemplary filter are indicated, in millimeters, on the drawing.

Transducer 104 is composed of two connection pads 110 and 112 for external wire connections, each integral with a respective conductive strip 114 or 116. Between strips 114 and 116 there is provided an interdigital electrode structure 118 which will be described with reference to FIG. 8a.

Similarly, transducer 106 includes two connection pads 120 and 122 for external wire connections, two conductive strips 124 and 126, and an interdigital electrode structure 128 which will be described with reference to FIG. 8b.

Isolating member 108 includes two connection pads 130 and 132, two conductive strips 134 and 136 and a metal grating 138 conductively connected between strips 134 and 136. The function of isolating member 108 is to lower RF feedthrough between transducers 104 and 106 and passband ripple due to propagation velocity differences between metal coated and uncoated surfaces of substrate 102. The thickness of the various metal electrodes was also selected to correct for velocity differences.

The electrical input to the filter is effected via pad 110, the electrical output via pad 122, and all other pads are connected to circuit ground.

According to one embodiment of the invention, each filter bank is composed of six filters, each having the form shown in FIG. 8 and each being in a respective case, arranged in a stack. Aternatively, three filters can be placed on each of two substrates or all six filters can be placed on a single substrate. It is believed that these arrangements will exhibit comparable performance.

Figure 8A:
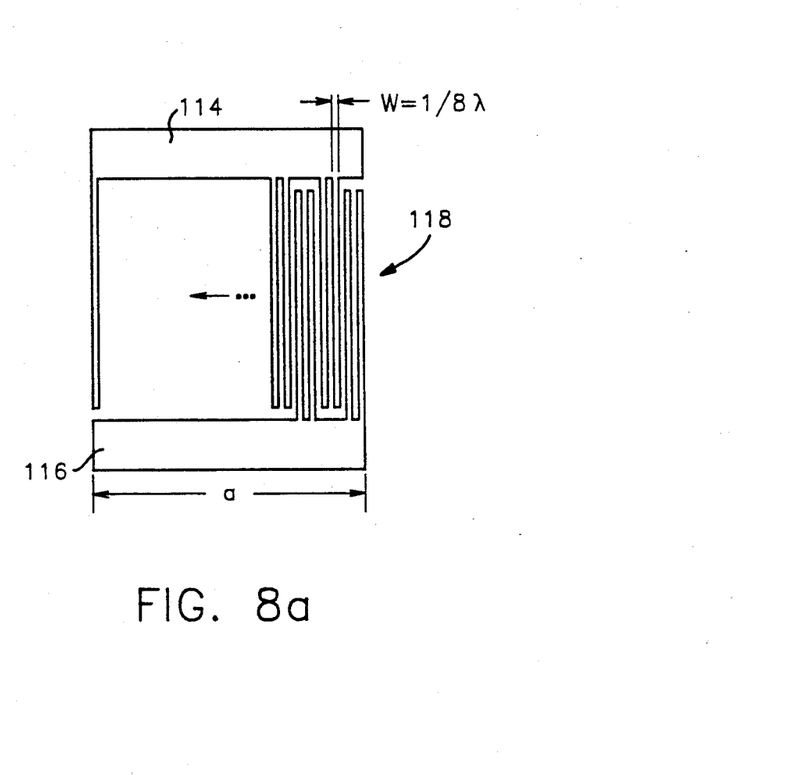
FIGS. 8a and 8b are plan views of portions of the filter of FIG. 8.

FIG. 8a illustrates one suitable form of electrode structure 118 of transducer 104. This structure is composed of spaced electrode finger pairs extending from each strip 114 and 116, with each electrode finger pair which extends from one strip being interposed between successive electrode finger pairs extending from the other strip. The electrode structure of FIG. 8a is unapodized. The electrode fingers of structure 118 have a width $W = \lambda/8$, where $\lambda$ is the wavelength of the acoustic wave in substrate 102 at the filter center frequency.

Figure 8B:
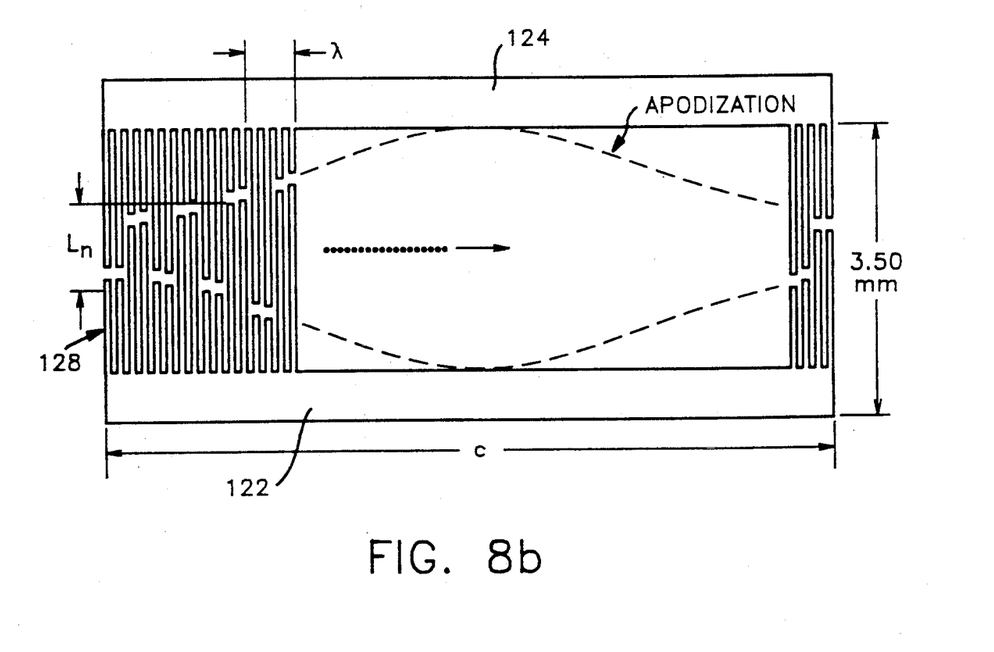

FIG. 8b is a similar view of the electrode structure 128 of transducer 106. In this structure, successive electrode finger pairs extending from each strip 122, 124 vary in length in a manner which increases to a maximum at the center of the structure. Each longer electrode finger pair which extends from one strip is interposed between longer pairs extending from the other strip and faces a shorter pair extending from the other strip. This structure is apodized in that the overlap, $L_n$, between adjacent longer pairs extending from respective strips 122, 124 varies along the length, c, of structure 128.

The value for $L_n$ and the total number of finger pairs in each transducer of each filter are determined by calculations performed by a CAD system.

Tables 1 and 2, below, provide relevant dimensions for a set of filters according to one preferred embodiment of the invention. All other dimensions would be determined on the basis of principles known in the art.

TABLE 1

Electrode width of SAW Filters

| Filter (#) | Center Frequency (MHz) | Wavelength λ (μm) | Electrode Width W (μm) |
| --- | --- | --- | --- |
| 1 | 72.0 | 43.8611 | 5.4826 |
| 2 | 73.2 | 43.1421 | 5.3998 |
| 3 | 74.4 | 42.4462 | 5.3058 |
| 4 | 75.6 | 41.7725 | 5.2216 |
| 5 | 76.8 | 41.1198 | 5.1400 |
| 6 | 78.0 | 40.4872 | 5.0609 |

TABLE 2

Actual length of IDT's of SAW Filters

| Filter (#) | Number of Finger Pairs Unapodized IDT | Number of Finger Pairs Apodized IDT | Actual IDT Length a (mm) | Actual IDT Length c (mm) |
| --- | --- | --- | --- | --- |
| 1 | 127 | 283 | 5.570 | 12.412 |
| 2 | 127 | 291 | 5.479 | 12.554 |
| 3 | 127 | 299 | 5.390 | 12.691 |
| 4 | 129 | 311 | 5.388 | 12.991 |
| 5 | 129 | 319 | 5.304 | 13.117 |
| 6 | 129 | 327 | 5.223 | 13.239 |

Final package dimensions for the complete six channel receiver part 4, exclusive of secondary coils 26 and 28, is 2.54×2.54×0.95 cm. Receiver system miniaturization will utilize hybrid microcircuit implementations and final "dense packaging" of the SAW filterbank and receiver into a hermetically sealed chronically implantable package. Concomitant packaging of the external transmitter part 2 which incorporates the existing Symbion speech processor will take advantage of SMD components.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A cochlear prosthesis comprising:
    a transmitter part arranged to be carried by a user and comprising:
    a sound-to-electrical signal transducer for deriving an electrical analog signal representative of incident acoustic signals in the audible frequency range;
    sound processing means connected to said transducer for dividing the electrical analog signal into a plurality of component signals;
    frequency modulating means connected to said sound processing means for deriving a plurality of frequency modulated signals each having a respectively different center frequency and each frequency modulated with a respective component signal;
    bandpass filter means composed of a plurality of first filter elements, each element being connected to receive a respective frequency modulated signal from said frequency modulating means and having a selected pass band centered on a respective center frequency of said frequency modulating means;
    frequency multiplexing means connected to said filter means for combining the signals passed by all of said filter elements; and
    transmitting antenna means connected to said frequency multiplexing means for emitting a radiation signal corresponding to the signals combined by said frequency multiplexing means; and
    a receiver part arranged to be surgically implanted in the user's body and comprising:
    receiving antenna means arranged to be positioned in proximity to said transmitting antenna means for converting the radiation signal emitted by said transmitting antenna means into a received signal corresponding to the signals combined by said frequency multiplexing means;
    frequency demultiplexing means including a plurality of second filter elements, said frequency demultiplexing means being connected to said receiving antenna means for causing each said second filter element to pass a respective portion of the received signal lying in a respective frequency band;
    demodulator and amplifier means connected to said frequency demultiplexing means for individually demodulating and amplifying the signal portion passed by each said second filter element; and
    a plurality of output electrodes each arranged to be implanted at a selected location in a cochlea of the user and each connected to said amplifier means for receiving a respective individually amplified received signal portion,
    wherein said first filter elements are surface acoustic wave filters.

2. A prosthesis as defined in claim 1 wherein said second filter elements are surface acoustic wave filters.

3. A prosthesis as defined in claim 2 wherein said frequency multiplexing means comprise a plurality of inductors connected to form a constant-k ladder circuit which is connected between said surface acoustic wave filters and said transmitting antenna means.

4. A prosthesis as defined in claim 2 wherein said transmitter part and said receiver part are composed entirely of analog signal circuits.

5. A cochlear prosthesis comprising:
    a transmitter part arranged to be carried by a user and comprising:
    a sound-to-electrical signal transducer for deriving an electrical analog signal representative of incident acoustic signal in the audible frequency range;
    sound processing means connected to said transducer for dividing the electrical analog signal into a plurality of component signals;
    frequency modulating means connected to said sound processing means for deriving a plurality of frequency modulated signals each having a respectively different center frequency and each frequency modulated with a respective component signal;
    bandpass filter means composed of a plurality of first filter elements, each element being connected to receive a respective frequency modulated signal from said frequency modulating means and having a selected pass band centered on a respective center frequency of said frequency modulating means;
    frequency multiplexing means connected to said filter means for combining the signals passed by all of said filter elements; and transmitting antenna means connected to said frequency multiplexing means for emitting a radiation signal corresponding to the signals combined by said frequency multiplexing means; and a receiver part arranged to be surgically implanted in the user's body and comprising: receiving antenna means arranged to be positioned in proximity to said transmitting antenna means for converting the radiation signal emitted by said transmitting antenna means into a received signal corresponding to the signals combined by said frequency multiplexing means;

frequency demultiplexing means including a plurality of second filter elements, said frequency demultiplexing means being connected to said receiving antenna means for causing each said second filter element to pass a respective portion of the received signal lying in a respective frequency band;

demodulator and amplifier means connected to said frequency demultiplexing means for individually demodulating and amplifying the signal portion passed by each said second filter element; and a plurality of output electrodes each arranged to be implanted at a selected location in a cochlea of the user and each connected to said amplifier means for receiving a respective individually amplified received signal portion, wherein said frequency modulating means comprise a plurality of phase locked loops each connected to derive a respective frequency modulated signal from a respective component signal.

6. A cochlear prosthesis comprising:

a transmitter part arranged to be carried by a user and comprising:

a sound-to-electrical signal transducer for deriving an electrical analog signal representative of incident acoustic signal in the audible frequency range;

sound processing means connected to said transducer for dividing the electrical analog signal into a plurality of component signals;

frequency modulating means connected to said sound processing means for deriving a plurality of frequency modulated signals each having a respectively different center frequency and each frequency modulated with a respective component signal;

bandpass filter means composed of a plurality of first filter elements, each element being connected to receive a respective frequency modulated signal form said frequency modulating means and having a selected pass band centered on a respective center frequency of said frequency modulating means;

frequency multiplexing means connected to said filter means for combining the signals passed by all of said filter elements; and transmitting antenna means connected to said frequency multiplexing means for emitting a radiation signal corresponding to the signals combined by said frequency multiplexing means; and a receiver part arranged to be surgically implanted in the user's body and comprising: receiving antenna means arranged to be positioned in proximity to said transmitting antenna means for converting the radiation signal emitted by said transmitting antenna means into a received signal corresponding to the signals combined by said frequency multiplexing means;

frequency demultiplexing means including a plurality of second filter elements, said frequency demultiplexing means being connected to said receiving antenna means for causing each said second filter element to pass a respective portion of the received signal lying in a respective frequency band;

demodulator and amplifier means connected to said frequency demultiplexing means for individually demodulating and amplifying the signal portion passed by each said second filter element; and a plurality of output electrodes each arranged to be implanted at a selected location in a cochlear of the user and each connected to said amplifier means for receiving a respective individually amplified received signal portion, wherein said frequency demultiplexing means comprise a plurality of inductors connected to form a constant-k ladder circuit which is connected between said receiving antenna means and said plurality of second filter elements.

* * * * *